United States Patent
Kao et al.

(10) Patent No.: US 6,855,112 B2
(45) Date of Patent: Feb. 15, 2005

(54) METHOD OF AND SYSTEM FOR HEALTH TREATMENT

(75) Inventors: Shang Ren Henry Kao, Hong Kong (CN); Ching Hui Goan, Hong Kong (CN)

(73) Assignee: The University of Hong Kong, Hong Kong (HK)

(*) Notice: Subject to any disclaimer, the term of this patent is extended or adjusted under 35 U.S.C. 154(b) by 66 days.

(21) Appl. No.: 10/074,617

(22) Filed: Feb. 12, 2002

(65) Prior Publication Data

US 2002/0156381 A1 Oct. 24, 2002

Related U.S. Application Data

(63) Continuation-in-part of application No. 09/616,801, filed on Jul. 14, 2000, now Pat. No. 6,375,622.

(51) Int. Cl.[7] .................................................. A61B 5/00
(52) U.S. Cl. .................... 600/300; 600/481; 600/485; 600/500; 600/549; 600/508; 600/587; 600/504
(58) Field of Search ............................... 600/300–301, 600/481, 485, 500–504, 549, 587, 591

(56) References Cited

U.S. PATENT DOCUMENTS

| | | | |
|---|---|---|---|
| 4,111,052 A | 9/1978 | Sniderman | |
| 4,624,262 A | 11/1986 | Berger et al. | |
| 4,825,874 A | 5/1989 | Uhlemann | |
| 4,971,059 A | 11/1990 | Niewald | |
| 5,215,097 A | 6/1993 | Watabe | |
| 5,447,167 A | 9/1995 | Fleischaker | |
| 5,964,720 A | 10/1999 | Pelz | |
| 6,375,622 B1 * | 4/2002 | Kao et al. | 600/485 |
| 6,406,426 B1 * | 6/2002 | Reuss et al. | 600/300 |

FOREIGN PATENT DOCUMENTS

DE   296 00 851 U1   6/1997

* cited by examiner

*Primary Examiner*—Robert L. Nasser
(74) *Attorney, Agent, or Firm*—Dickstein, Shapiro, Morin & Oshinsky, LLP.

(57) ABSTRACT

The present invention relates to a method of and a system for treating a health condition of a user. The method includes determining a sensory signal for use to treat the user's health condition, measuring the change to the sensory signal while the user is engaging in an activity, and using the sensory signal change to regulate the user's activity to thereby treat the user's health condition. The system has a sensor device for measuring a sensory signal of the user while the user is engaging in an activity and a display device receiving the sensory signal measured by the sensor device and displaying the sensory signal. The change to the sensory signal is used to regulate the user's activity to thereby treat the user's health condition.

18 Claims, 2 Drawing Sheets

METHOD OF AND SYSTEM FOR HEALTH TREATMENT

CROSS REFERENCE

This is a continuation-in-part of U.S. patent application Ser. No. 09/616,801 filed Jul. 14, 2000 now U.S. Pat. No. 6,375,622.

FIELDS OF THE INVENTION

The present invention relates generally to a method of and a system for health treatment. In particular, the present invention relates to a method of and a system for behavior, psychosomatic, and psychiatry treatment, special education, rehabilitation, and clinical and health psychology.

BACKGROUND OF THE INVENTION

Chinese calligraphy, a traditional Chinese art with a history of several thousand years, is practiced by millions of people in Asia. In addition to the artistic value of Chinese calligraphy, recent psychological research has established that Chinese calligraphy is capable of achieving, in the course of its execution, emotional stabilization, mental relaxation, and physiological slowdown from the physical perspective. From the cognitive perspective, research has confirmed that Chinese calligraphy has positive impacts on heightened attention and concentration, enhanced problem solving capabilities of spatial abilities, improved spatial and abstract reasoning, shortened response time, and improved short-term memory. For the general population, Chinese calligraphy has been found to be capable of enhancing the general health condition of the practitioner.

Biofeedback training refers to clinical training procedures used to modify a user's physiological responses or patterns of such responses that aim to achieve self-regulation of maladaptive responses and disordered states. The procedures enable the user to control a certain specified physiological process by providing an external cue or a monitor to indicate the activity of the physiological process. Biofeedback represents the prototypical approach of the discipline of "behaviourial medicine." Within behavioral medicine, biofeedback is one clinical technique among many others, which have been introduced as interventions for health disorders.

The principles of biofeedback have also been applied to products and instruments used for ordinary practice and training by healthy individuals. When applied to users without health disorders, biofeedback can enhance self-regulation of bodily processes to thereby improve general health, such as the generation of specific patterns of brain waves in the practice of transcendental meditation. Therefore, biofeedback training offers an effective process of treating illnesses as well as enhancing the health of the user under a system of feedback regulation of bodily states.

It would be desirable to provide a handwriting training for intervening a number of psychosomatic, behaviourial, and psychological disorders, such as essential hypertension, type II diabetes, emotional conditions in mental patients, attention deficit and hyperactivity, and mild mental retardation. It would also be desirable to provide a handwriting training that is not limited by any type of written language, but are general and universal for health improvement, and therapeutic and rehabilitative intervention. Further, it would also be desirable to integrate the handwriting and the biofeedback training into a biofeedback system for self-regulation during the handwriting process for health and clinical intervention.

SUMMARY OF THE INVENTION

The present invention relates to a method of and a system for treating a health condition of a user. The method of the present invention comprises determining a sensory signal for use to treat the user's health condition. The sensory signal can be determined in accordance to the health condition to be treated. The method also comprises measuring the change to the sensory signal while the user is engaging in an activity. The change of the sensory signal can be used as a biofeedback to regulate the user's activity and thereby to treat the user's health condition.

The system of the present invention comprises a sensor device for measuring a sensory signal of the user while the user is engaging in an activity. The sensory signal can be determined in accordance to the health condition to be treated. The system can also comprise a display device that can receive the sensory signal measured by the sensor device and display the sensory signal. The change to the sensory signal can be used to regulate the user's activity to thereby treat the user's health condition.

According to one aspect of the invention, the sensory signal can be measured when the user is engaging in a graphic production. The graphic production can be made based on a predetermined graphic element of the present invention.

BRIEF DESCRIPTION OF THE DRAWINGS

These and other features, aspects, and advantages of the present invention will become much more apparent from the following description, appended claims, and accompanying drawings, in which:

DETAILED DESCRIPTION OF THE PREFERRED EMBODIMENTS

Figure 1:
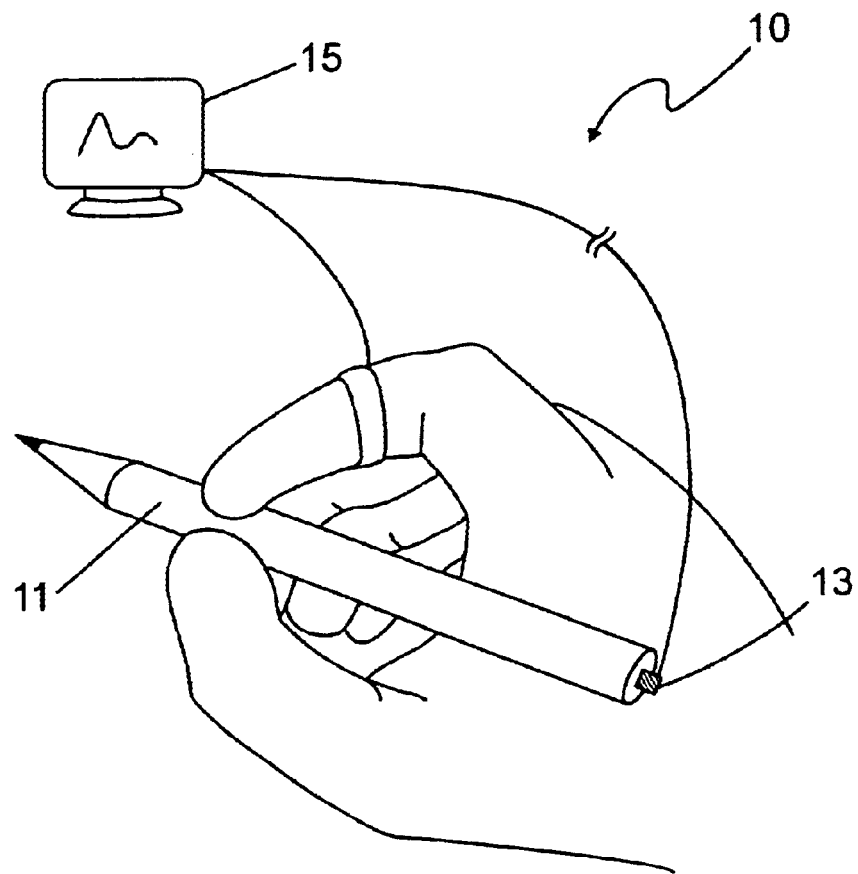
FIG. 1 shows an embodiment of a treatment system formed according to the principles of the present invention.
Figure 2:
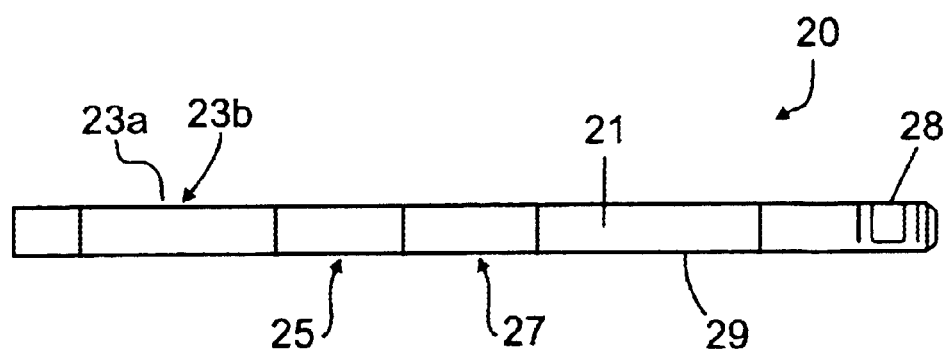
FIG. 2 shows another embodiment of the treatment system formed according to the principles of the present invention.
Figure 3:
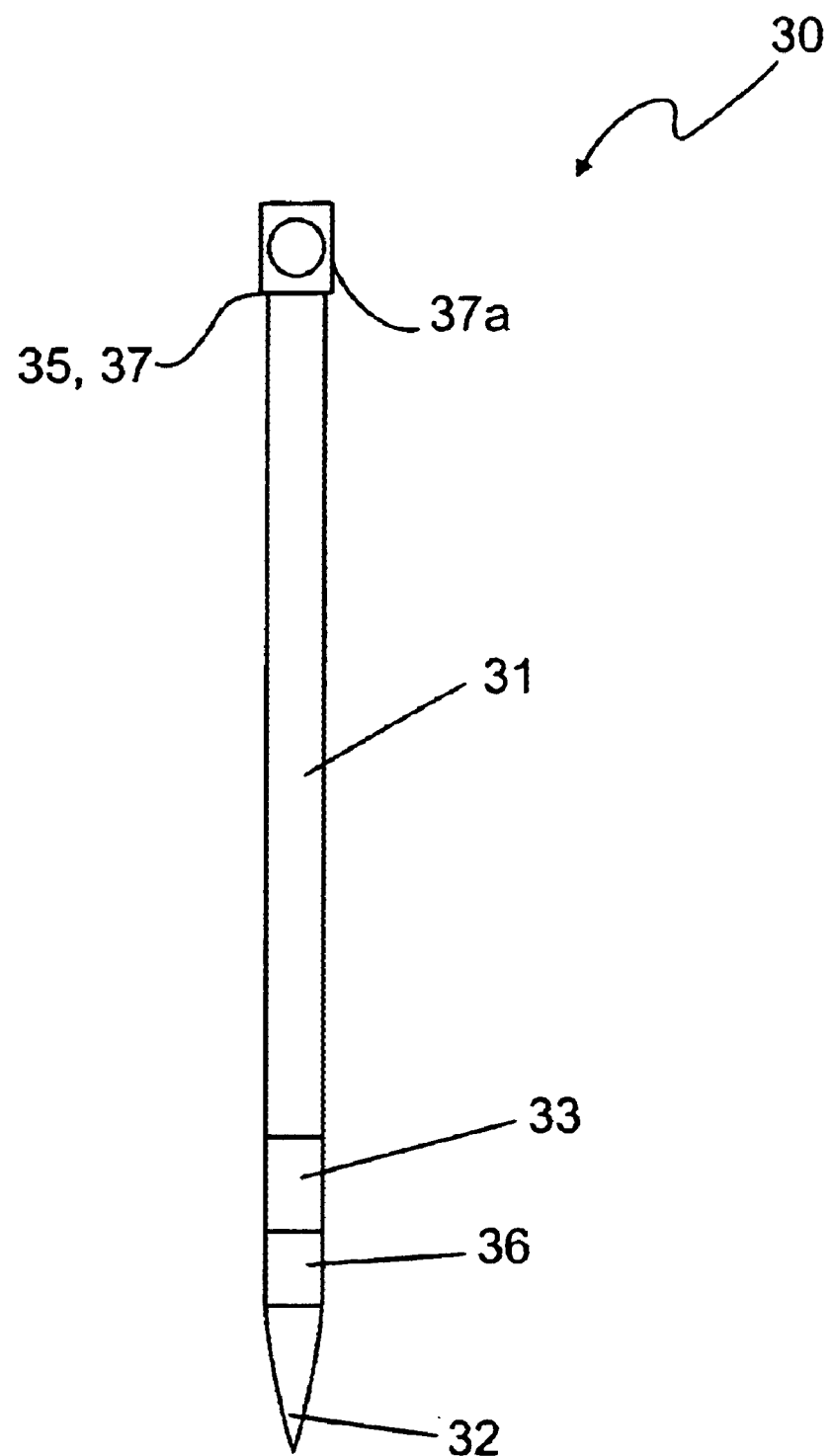
FIG. 3 shows a treatment system of the present invention with an embedded spirit-level gauge on the article.

Various treatment methods and systems embodying the principles of the present invention are illustrated in FIGS. 1 to 3. The present invention employs the biofeedback principle to regulate a user's bodily activities for purpose of treating a health condition. The methods and systems of the present invention are capable of measuring a sensory signal from the user and use the measured sensory signal to regulate the user's bodily activities to thereby treat the user's health condition. In the present invention, the treatment of a health condition can refer to treatment of various physical diseases and/or mental disorders of a patient, rehabilitation of behavioral, physical, mental, psychosomatic, and/or emotional deficiency of an impaired individual, and/or enhancement of general health of a healthy individual. In the following embodiments, same elements are designated with reference numerals having the same last digits and repetitive descriptions are omitted.

According to one aspect of the invention, a treatment system is provided to treat various health conditions of the user. The treatment system of the present invention can comprise a sensor device for measuring a sensory signal of the user. The sensory signal can be so determined that it is capable of reflecting a health condition to be treated. Exemplary sensory signals can include, but not limited to, blood pressure, digital pulse volume, electroencephalogram, electrocardiogram, electromyogram, galvanic heart rate, pulse rate, respiration, skin conductance, skin response, and skin temperature. Depending on the health condition to be treated, one or more sensory signals can be used, which can either independently or collectively reflect the user's health condition for purpose of treatment. In one embodiment, a plurality of sensory signals can be used for treating the same health condition of the user.

The treatment system can also comprise a display device which can receive the sensory signal measured by the sensor device and display the sensory signal. The change to the sensory signal can be used to regulate the user's activity and thus treat the user's health condition. The display device can be adapted to display the measured sensory signal in various formats. For example, the measured sensory signals can be displayed as at least one of visual, auditory, tactile, and thermal signals. It will be appreciated that other forms of display are also within the scope of the invention.

The treatment system can also comprise an article to be used by the user when engaging in the bodily activity. In one embodiment, the article can be adapted to be held by the user in the bodily activity. Examples of the article can include, but are not limited to, writing instruments (e.g., various pens and Chinese writing brushes), personal care devices (e.g., toothbrushes and shavers), exercise devices, computer mouses, joy sticks, medical devices, hand-craft devices, household utensils (e.g., cooking and cleaning utensils), hand-tools (e.g., hammers and screw drivers), and any combination thereof. Writing instruments can have various tip stiffness (e.g., hard tips, resilient tips, and soft tips), tip size, tip shape, or other tip physical features. Exemplary writing instrument can include, but are not limited to, various pens (e.g., pencils, ball-point pens, fountain pens, sign-pens, and calligraphy pens), brushes (e.g., writing brushes and paint brushes), stylus, chalks, crayons, markers, and the like.

Optionally, the treatment system can comprise one or more graphic elements, which can be used by the user to compose a graphic production containing the graphic element. The graphic element can be selected based on its visual complexity, such as the number strokes of a character. Exemplary graphic element can include, but not limited to, characters (e.g., Chinese characters), alphabets (e.g., English alphabets), scripts, numerals, geometric units (e.g., linearity, curvature, angularity, circle, square, closure, symmetry, and parallelism), non-linguistic forms (e.g., drawings, cave writings, tokens, logos, icons, and symbols), and any combination thereof. The graphic elements can be provided on any media forms, such as paper, board, glass, other two-dimensional surface and three-dimensional space.

According to another aspect of the invention, the treatment method is provided to treat various health conditions of the user. Depending on the health condition to be treated, one or more sensory signals can be used, which can either independently or collectively reflect the health condition of the user, to thereby facilitate the treatment. The treatment method can comprise monitoring a sensory signal of the user while the user is engaging in a bodily activity. The sensory signal measured can then be used as a feedback information to regulate the user's bodily activity to afford treatment to the user's health condition. In one embodiment, the measured sensory signal can be a biofeedback or a neuro-feedback. Such a biofeedback or a neuro-feedback can facilitate the user or a medical personal to regulate the user's bodily activity to thereby alleviate the health condition.

The treatment of the health condition can be carried out when the user is engaging in various bodily activities. The bodily activities can be performed in various manners, such as on a two-dimensional surface or in a three-dimensional space. Exemplary bodily activities can include, but are not limited to handwriting (e.g., writing, drawing, and painting), personal caring (e.g., brushing teeth and shaving), medical caring, exercising, hand-crafting (e.g., sewing and knitting), and household activities (e.g., cooking and cleaning). In one embodiment, the present invention is used to regulate the user's handwriting activity. The handwriting activity can comprise one or more of tracing a graphic element, copying a graphic element, and free handwriting (e.g., free writing, free drawing, and free painting). In an exemplary embodiment, the handwriting activity can comprise tracing a graphic element, copying a graphic element, and free handwriting performed in that order. In another embodiment, the handwriting activity can involve the use of a Chinese writing brush as will be described below.

The present invention can be formed to serve various purposes. For example, the present invention can be used to improve the user's general health, emotional stabilization, cognitive activation, and muscular control efficiency. Additionally or alternatively, the present invention can be used to treat diseases. Accordingly, the treatment system and method of the present invention can be formed to target at specified categories of health conditions to be treated. For example, the specific functions of the present invention can vary to therefore serve various behavioral dimensions of the users. For each of the dimensions identified, various biofeedback mechanism can be employed for the purpose of treatment as will be described below.

According to one aspect of the present invention, the treatment system and method can be formed to improve the general health of the user. In one embodiment, the display can comprise biofeedback of the user's bodily conditions that are useful and helpful to promote the user's general health. In an exemplary embodiment, one or more sensory signals can be measured in the course of the bodily activity, such as handwriting activity. The sensory signals can be one or more of the pulse rate, blood pressure, digital pulse volume, skin conductance, skin temperature, heart rate and pulse rate of the user.

According to another aspect of the present invention, the treatment system and method can be formed to stabilize the user's emotion. In one embodiment, the display can comprise biofeedback information about the user's bodily conditions helpful for enhancing the emotional stability, reducing anxiety, and positively increasing mood conditions. In an exemplary embodiment, the sensory signals to be measured in the course of the bodily activity, such as handwriting activity. The sensory signal can be one of more of galvanic skin response, digital pulse volume, skin temperature, skin conductance, blood pressure, pulse rate and heart rate.

According to another aspect of the present invention, the treatment system and method can be formed to improve the user's cognitive activation. In one embodiment, the sensory signal used for this purpose can be electroencephalogram. In an exemplary embodiment, the sensor device can monitor various states of specific and selected patterns of electroencephalographic activities of the user during the bodily activity, such as handwriting process. The selected brain wave patterns can reflect higher states of cognitive functions associated with creativity, memory, attention, and problem solving.

According to another aspect of the present invention, the treatment system and method can be formed to improve muscular control efficiency. In one embodiment, the display device can display conditions of the user's motoric or muscular control of the bodily act, such as a writing act. The display can be used as a feedback to enable the user to conduct proper or corrective manipulative and transport movements for efficient bodily activity, such as handwriting tasks. In an exemplary embodiment, the sources of the biofeedback can be derived from the motor activities of the user relative to certain practical conventions or behavioral criteria that are associated with good penmanship. The present invention can therefore aid and help learning, training, as well as corrective or rehabilitative remediation for good penmanship and graphic skills.

The features of the present invention can be better understood through the following description of various embodiments. The following exemplary embodiments are used to demonstrate the innovative merits of the invention and its potential development within the general concept of a biofeedback based treatment system and method for health enhancement and therapy.

FIG. 1 shows a treatment system 10 formed according to the principle of the present invention. The treatment system 10 can comprise an article 11 to be used by the user in the course of a bodily activity. The physical features of the article 11, such as weight, size, length, and surface texture, can depend on the composition of component parts and associated design considerations. In one embodiment, the biofeedback training is incorporated in the handwriting activity, such as Chinese brush handwriting, for self-regulating bodily activities associated with the handwriting activity. The present invention can provide the most effective health and therapeutic functions when integrating the biofeedback principle with the principles of Chinese brush handwriting to thus form a comprehensive biofeedback brush-writing treatment system. In such an embodiment, the article 11 can be a Chinese writing brush as shown in FIG. 3. It will be appreciated that other articles 11 are also within the scope of the invention.

The treatment system 10 can also comprise a sensor device 13, such as a physiological monitoring and sensing device. The sensor device 13 can be adapted to measure at least one sensory signal, which reflects the state of the user's behavioral, mental, and/or physiological changes during handwriting or drawing. The sensor device 13 of the treatment system 10 can be formed in various manners. In an exemplary embodiment, the sensor device 13 can be attached to the article 11, such as a writing instrument. For example, the sensor device 13 can be built in the article 11. In another exemplary embodiment, the monitoring can be made through an external sensor device 13. In an exemplary embodiment, the external sensor device 13 can be a strap, a ring, or the like. Such external sensor devices 13 can be attached to the article 11 depending on the type of feedback required by the user.

Additionally or alternatively, the treatment system 10 can comprise a sensor device 13 externally linked to the article 11. This external sensing device 13 allows more flexible application of sensing electrodes to measure bio-indicators, such as heart rate, blood pressure, or pulse rate. In an exemplary embodiment, the sensor device 13 can be a finger strap 14 with electrode or a set of electrodes (not shown) which can be attached to relevant parts of the user's body. The external sensing device 13 may also be integrated with larger or more advanced biological recording system (not shown) for more varied display of biofeedback for the bodily activity, such as brush handwriting training. It will be appreciated that other forms of the sensor device 13 are also with the scope of the invention.

The treatment system 10 of the present invention can also comprise a display device 15, which is capable of displaying changes in the user's sensory signal occurred during the user's bodily activity, such as handwriting. The display can be carried out through various display signals, such as visual signals (e.g., diagram and color), auditory signals (e.g., voice message and tone), tactile signals, and/or thermal signals (e.g., skin temperature). The display signals can indicate the user's bodily conditions, which in turn can reflect the user's behavioral, mental, and physiological changes occurred during the bodily activity. The user can then use the display signal as a feedback information to facilitate changes in the bodily activity, such as through conscious control of the bodily activity, to thereby affect the health condition treatment.

In one embodiment where the user is engaging in a handwriting activity, the display device 15 can employ one or more display signals to indicate the changes in the user's blood pressure, digital pulse volume, skin conductance, skin temperature, heart rate and/or pulse rate occurred during the handwriting activity. Such display functions as a feedback information for the user or other medical personal to regulate the user's handwriting activity. For example, when the display signal shown on the display device 15 indicate that one or more of the blood pressure, digital pulse volume, skin conductance, skin temperature, heart rate and pulse rate increase, the user is informed of the change in the bodily condition. Accordingly, the user can consciously slow down the handwriting activity in an effort to reduce the blood pressure, digital pulse volume, skin conductance, skin temperature, heart rate and/or pulse rate.

The display device 15 can be formed in various manners. In one embodiment, the display device 15 can comprise a monitor device, which is adapted to receive the sensory signal measured by the sensor device 13. In an exemplary embodiment, the display device 15 can comprise a computer, which is capable of displaying one or more display signals simultaneously. In another embodiment, the display device 15 can be embedded in or otherwise integrated with the writing instrument 11. It will be appreciated that other types of the display device 15 are also with the scope of the invention.

FIG. 2 shows another treatment system 20 formed according to the principle of the present invention. In an exemplary embodiment, the treatment system 20 can comprise an article 21, such as a writing instrument, to be used by the user in the course of a bodily activity, such as handwriting. The treatment system 20 can also comprise a sensor device 23, and a display device 25. In one embodiment, the display device 25 can comprise a feedback unit 27. One of more of the sensor device 23, the display device 25, and the feedback mechanism 27 can be either embedded in or external to the article 21. In an exemplary embodiment such as shown in FIG. 2, at least one of the sensor device 23 and the display device 25 can be embedded in the article 21. It will be appreciated that other formation of the sensor device 23 and display device 25 are also within the scope of the invention.

The sensor device 23 can comprise a bio-sensor 23a embedded in the article 21 or a bio-sensor 23b externally linked to the article 21, such as through wires, depending on the type of the article 21. The sensor device 23 can be formed to measure one or more of the many available physiological indices from the user during the bodily activity, such as a writing activity. In an exemplary embodiment, the sensor device 23 can comprise an electrode. The available sensory signals can include, but not limited to, blood pressure, digital pulse volume, electroencephalogram, electrocardiogram, electromyogram, galvanic heart rate, pulse rate, respiration, skin conductance, skin response, skin temperature, and any combination thereof. The type of sensory signals to be used in connection with a given article 21 depends upon the functions to be served by the particular article 21.

The display device 25 can receive and display the sensory signal measured by the sensor device 23. In one embodiment, the feedback unit 27 can receive and transmit the captured sensory signals to the display device 25. According to the invention, the display device 25 displays the sensory signal of the user as a feedback for the user to self-regulate the bodily activity. The display can be conducted through one or more of the display signals, such as visual, auditory, and thermal signals. In one embodiment, the visual signals may be displayed in the form of color codes in singular or multiple colors. In another embodiment, the auditory signals can be displayed by a tonal code. In a further embodiment, the thermal signals can be displayed by skin temperature.

Optionally, the treatment system 20 can comprise a power supply unit 29. The power unit 29 can enable the operation of the sensor device 23, the display device 25, and the feedback unit 27, if there is one. In an exemplary embodiment, the power unit 29 can comprise suitable micro batteries. The power unit 28 can be embedded in or external to the article 11.

In a first embodiment, the treatment system 20 can be formed to treat the general health of a user. In such a general health treatment system, the sensor device 23 can be a bio-sensor, which can be built-in the article 21 or externally linked to the article 21. The sensor device 23 can measure various sensory signals, such as blood pressure, digital pulse volume, skin conductance, skin temperature, heart rate, and/or pulse rate, thus forming different models of the general health treatment system 20. Additional or alternative sensor device 23 can be used to detect other physiological states to thereby form additional models of the general health treatment system 20.

The display device 25 for a general health treatment system 20 can be adapted to display the sensory signals through various display signals, such as visual, auditory or thermal signals. The display signals can be used individually or collectively. For example, the visual feedback can use color codes, such as yellow, amber, and green, to reflect the extent of the physiological changes in a continuously changing mode. Additionally or alternatively, the visual feedback can be displayed by the intensity or dimming of colored light indicator or other optional visual display mechanisms. In another exemplary embodiment, the auditory feedback can employ an audible tone, such as a free-flow up-down configuration, or any variations. In a further exemplary embodiment, the thermal display can be continuous thermal signals varying in temperature from the article 21 in a continuous changing and up-down mode.

Optionally, the power unit 28 for the general health treatment system 20 can comprise the latest technology in microelectronics. In an exemplary embodiment, the tiniest possible power cells can be adopted for operating the sensor device 23 and the display device 25 of the treatment system 20.

In a second embodiment, the treatment system 20 can be formed to improve the emotional health of a user. In one exemplary embodiment, the sensor device 23 of the emotional health treatment system 20 can comprise a built-in electrode 23. The sensor device 23 can measure one or more of the digital pulse volume, skin temperature, skin conductance, blood pressure, pulse rate and heart rate, forming different separate models of the emotional health treatment system 20. Additional or alternative sensor device 23 can be used to measure other physiological states thereby forming additional modes of the emotional health treatment system 20. In another exemplary embodiment, the sensor device 23 can be externally linked to the article 21 for detecting sensory signals from the user. For example, such external sensor device 23 can be a finger strap or a set of electrodes (not shown). In addition to the above bio-sensory measurement modes, the external sensor device 23 can allow more flexible use of other sensory modalities, such as skin conductance, and heart rate. The external sensor device 23 can also be linked to large polygraphic recording equipments for more sophisticated sensing and monitoring requirements on bodily condition changes. In a further exemplary embodiment, the sensor device 23 can be a thermometric detector. For example, the thermometric detector 23 can be embedded in the article 21 for recording the changes of skin temperature of the user in the course of bodily activity. It will be appreciated that other forms of sensor devices 23 are also within the scope of the invention.

The display signals used for the emotional health treatment system 20 can be visual, auditory, or thermal display signals. In one exemplary embodiment, the visual display can be in the form of diagram or color coding, such as yellow, amber, red, flashing light. In another exemplary embodiment, the auditory display can be in the form of voice messages or audible tones. In a further exemplary embodiment, the thermal display can be in the form of varying temperature. For example, the display device 25 can display the user's body temperature in the form of an analog or digital signal as two separate models. In one embodiment, the display device 25 can be embedded in the article 21. The thermometric detector 23 and the display device 25 can be combined to carry out the sensing and displaying functions, similar to a thermometer. As a result, the emotional health treatment system 20 is capable of using any readily available thermometric devices, instead of color codes, for visual display. It will be appreciated that other forms of display devices 25 are also within the scope of the invention.

In a third embodiment, the treatment system 20 can be formed to improve the cognitive health of a user. The cognitive health treatment system 20 can measure electroencephalograph activities of the brain to reflect the various states of cognition associated with the user's bodily activity. Since different sites of the cortex are responsible for different dimensions of behavior, the selected sites can be linked externally as well as singularly to the article 21. Thereby, the electroencephalograph signals from a given site can be the feedback information relayed back to the user for purpose of regulating bodily activity. Common sites in connection with human cognitive activities include P3, P4, C3, C4, T3, and T4, where different patterns of the brain waves will reflect different cognitive functions. Beta waves are found to relate to the active alertness and arousal, while alpha waves reflect a state of the mind with the most creative cognitive outcomes take place.

The sensor device 23 can be a single wave electrode 23. The single wave electrode 23 can be externally linked to the article 21. Single wave electrode measurement is available so that specific functions served by the wave pattern become the source for feedback information. The single wave electrode 23 forms the external basis of a given model of the cognitive health treatment system 20. There can be as many models of the cognitive health treatment system 20 as there is the variety of wave patterns associated with the cognitive functions. This cognitive health treatment system 20 can be attached to a multi-channel polygraph recorder for more advanced feedback training with this special cognitive health treatment system 20.

The display device 25 of the cognitive health treatment system 20 can use various display signals. In one exemplary embodiment, the display signal can be color coding, such as yellow, amber, red, or flashing light. In another exemplary embodiment, the display signal can be auditory signal, such as an up-down tone. In a further exemplary embodiment, the display signal can be thermal signals as discussed above.

FIG. 3 shows a further treatment system 30 formed according to the principle of the present invention, which can be formed to improve the motor efficiency of a user. In an exemplary embodiment, the article 31 of motor efficiency treatment system 30 can be a Chinese writing brush with a soft writing tip. For the brush handwriting especially, the ability to maintain vertical position of the writing brush 31 is one essential component to the attainment of attention and facilitation of task concentration. This rigid motor control is also essential in the traditional calligraphic training, which is closely linked to the elevation of emotional stability. The motor efficiency treatment system 30 comprises a spirit-level gauge as a feedback unit 37. In an embodiment, the spirit-level gauge 37 is preferably embedded in the shaft of the writing brush 31. In another embodiment, the spirit-level gauge 37 can be mounted on the opposite end of the tip 32. The spirit-level gauge 37 can display visual feedback information regarding the degree of motor control efficiency of the user with reference to the verticality of the writing brush 31 relative to the writing surface. In a preferred embodiment, the spirit-level gauge 37 can comprise a sealed bubble 37a, which by its very nature can indicate the extent of the vertical alignment of the writing brush 31 relative to the writing surface. In a more preferred embodiment, the bubble 37a can be color-coded for an easy recognition and monitoring during the writing process.

In another embodiment, the article 31 of the motor efficiency treatment system 30 can be a writing instrument having a hard-tip. The sensor device 33 of the motor efficiency treatment system 30 can comprise a pressure transducer. The pressure transducer 33 can be embedded in the lower section of the writing instrument 31, which responds to the pressure exerted thereto by the user. This pressure information is recorded by the transducer 33 and fed back and displayed by the display device 35 in visual or auditory signals. The visual displays can be color-coded lights in multiple discrete modes or one color-code with differing light intensity. Additionally or alternatively, the display can be auditory signals, such as a continuous or constant tone varying in pitch, one continuous tone with rising and falling pitch sound to reflect the magnitude of the force exertion on the instrument by the user, or discrete tones showing multiple levels of sound to reflect the pressure exerted by the user.

The writing instrument 31 of the motor efficiency treatment system 30 is mainly designed to have a hard-tip. Accordingly, the tip pressure can easily measured by the pressure transducer 33. However, the design can also be applied to a writing brush having a relatively stiff soft-tip. The essence of this embodiment is to caution the user of the excessive force exerted onto the writing instrument 31 to thereby reduce fatigue and prevent development of callous and cramps in the user's hand and fingers due to sustained exertion of force in the course of the writing act.

In a further embodiment, the article 31 of the motor efficiency treatment system 30 can be employed to produce a 3-D or 3-D like movement. For example, a hard tip writing instrument 31 can be formed so that the hard tip can retract, or otherwise yield, in response to the pressure exerted thereon by the user. As a result, a hard-tip writing instrument 31 can write like a soft-tip brush. Ultimately, the user will be able to enjoy many of behavioral benefits in the user's cognitive, emotional, perceptual, motor, and physiological changes from writing with such a writing instrument 31.

The retractable property of a hard-tip writing instrument 31 can be achieved by various means such as a retractable mechanism 36. The retractable mechanism 36 can be embedded in the writing instrument 31, such as just above the tip portion thereof. The retraction magnitude of the tip 32 can depend on the elasticity degree of the tip desired. In a preferred embodiment, the retractable mechanism 36 can have plural grades of elasticity. The feedback provided to the user with respect to the elasticity level can be just the natural kinesthetic information from the movement of the tip 32 and/or the writing instrument 31. Therefore, it is not necessary for further elaboration of visual or auditory displays. The embodiment can incorporate some of the design features of the above embodiments.

It will be appreciated that the various features described herein may be used singly or in any combination thereof. Therefore, the present invention is not limited to only the embodiments specifically described herein. While the foregoing description and drawings represent a preferred embodiment of the present invention, it will be understood that various additions, modifications, and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiment is therefore to be considered in all respects as illustrative and not restrictive, the scope of the invention being indicated by the appended claims, and not limited to the foregoing description.

What is claimed is:

1. A method of regulating the mental or psychosomatic condition of a user, comprising:

providing a graphic element for the user to compose a graphic production comprising the graphic element;

determining a sensory signal for use to treat the user's health condition; measuring a change of the sensory signal while the user is composing the graphic production; and using the sensory signal change to regulate the user's activities in composing the graphic production to thereby regulate the mental or psychosomatic condition to improve the user's health.

2. The method of claim 1, wherein the sensory signal is determined in accordance to the health condition to be treated.

3. The method of claim 2, wherein the sensory signal is at least one of blood pressure, digital pulse volume, skin conductance, skin temperature, heart rate and pulse rate when the health condition is the user's general health.

4. The method of claim 2, wherein the sensory signal is at least one of digital pulse volume, skin temperature, skin conductance, blood pressure, pulse rate and heart rate when the health condition is the user's emotional health.

5. The method of claim 2, wherein the sensory signal is electroencephalogram when the health condition is the user's cognitive health.

6. The method of claim 1, wherein the sensory signal is selected from the group consisting of blood pressure, digital pulse volume, electroencephalogram, electrocardiogram, electromyogram, galvanic heart rate, pulse rate, respiration, skin conductance, skin response, skin temperature, and any combination thereof.

7. The method of claim 1, wherein the graphic element is selected from the group consisting of characters, alphabets, scripts, numerals, geometric units, non-linguistic forms, and any combination thereof.

8. The method of claim 1 further comprising determining a second sensory signal, and displaying the second sensory signal while the user is composing the graphic production.

9. The method of claim 8 further comprising displaying the sensory signals in at least one of the forms of visual, auditory, tactile, and thermal signals.

10. The method of claim 1, wherein the change in the sensory signal is measured when the user is engaging in a handwriting activity.

11. The method of claim 10, wherein the handwriting activity comprising tracing a graphic element.

12. The method of claim 10, wherein the handwriting activity comprising copying a graphic element.

13. The method of claim 10, wherein the handwriting activity comprising tracing a graphic element, copying a graphic element, and free handwriting.

14. The method of claim 1 wherein the change in the sensory signal is measured when the user is engaging in a free handwriting.

15. The method of claim 1, wherein the change in the sensory signal is measured when the user is handwriting a graphic element.

16. The method of claim 15, wherein the graphic element is selected from the group consisting of characters, alphabets, scripts, numerals, geometric units, nonlinguistic forms, and any combination thereof.

17. The method of claim 15, wherein the graphic element comprises a predetermined non-linguistic form.

18. The method of claim 17, wherein the non-linguistic form is selected from the group consisting of drawings, cave writings, tokens, logos, symbols, and any combination thereof.

* * * * *